United States Patent
Park et al.

(10) Patent No.: US 9,041,416 B2
(45) Date of Patent: May 26, 2015

(54) PHYSICAL PROPERTY SENSOR WITH ACTIVE ELECTRONIC CIRCUIT AND WIRELESS POWER AND DATA TRANSMISSION

(75) Inventors: Jin Woo Park, Suwanee, GA (US); Florent Cros, Decatur, GA (US); Mark G. Allen, Atlanta, GA (US)

(73) Assignee: St. Jude Medical Luxembourg Holdings II S.à.r.l., Luxembourg (LU)

( * ) Notice: Subject to any disclaimer, the term of this patent is extended or adjusted under 35 U.S.C. 154(b) by 354 days.

(21) Appl. No.: 13/588,518

(22) Filed: Aug. 17, 2012

(65) Prior Publication Data
US 2012/0313649 A1  Dec. 13, 2012

Related U.S. Application Data

(63) Continuation of application No. 12/506,170, filed on Jul. 20, 2009, now Pat. No. 8,264,240.

(60) Provisional application No. 61/082,207, filed on Jul. 20, 2008.

(51) Int. Cl.
*A61B 19/00* (2006.01)
*A61B 5/00* (2006.01)
*H02J 7/02* (2006.01)

(52) U.S. Cl.
CPC ....... *A61B 5/0031* (2013.01); *A61B 2560/0219* (2013.01); *H02J 7/025* (2013.01)

(58) Field of Classification Search
USPC .................................................. 324/652, 658
See application file for complete search history.

(56) References Cited

U.S. PATENT DOCUMENTS

| 7,276,703 | B2 * | 10/2007 | Berkcan et al. | 250/358.1 |
| 2005/0140212 | A1 * | 6/2005 | Hamel et al. | 307/44 |
| 2009/0105557 | A1 * | 4/2009 | Najafi et al. | 600/301 |

* cited by examiner

*Primary Examiner* — Vincent Q Nguyen
(74) *Attorney, Agent, or Firm* — Ballard Spahr LLP (57) ABSTRACT

Wireless sensors configured to record and transmit data as well as sense and, optionally, actuate to monitor physical properties of an environment and, optionally, effect changes within that environment. In one aspect, the wireless sensor can have a power harvesting unit; a voltage regulation unit, a transducing oscillator unit, and a transmitting coil. The voltage regulation unit is electrically coupled to the power harvesting unit and is configured to actuate at a minimum voltage level. The transducing oscillator unit is electrically coupled to the voltage regulation unit and is configured to convert a sensed physical property into an electrical signal. Also, the transmitting coil is configured to receive the electrical signal and to transmit the electrical signal to an external antenna.

38 Claims, 9 Drawing Sheets

PHYSICAL PROPERTY SENSOR WITH ACTIVE ELECTRONIC CIRCUIT AND WIRELESS POWER AND DATA TRANSMISSION

This application is a continuation of U.S. patent application Ser. No. 12/506,170, filed Jul. 20, 2009, which claims priority to and the benefit of U.S. Provisional Application No. 61/082,207, filed Jul. 20, 2008, which applications are incorporated in their entirety in this document by reference.

SUMMARY

In various aspects, the wireless sensor s described herein are configured to record and transmit data as well as sense and, optionally, actuate to monitor physical properties of an environment and, optionally, effect changes within that environment. In one aspect, the implantable wireless sensor can comprise a power harvesting unit; a voltage regulation unit, a transducing oscillator unit, and a transmitting coil. The voltage regulation unit is electrically coupled to the power harvesting unit and is configured to actuate at a minimum voltage level. The transducing oscillator unit is electrically coupled to the voltage regulation unit and is configured to convert a sensed physical property into an electrical signal. Also, the transmitting coil is configured to receive the electrical signal and to transmit the electrical signal to an external antenna.

Optionally, the wireless sensor can be configured to delay the energizing the voltage regulation unit until a predetermined time delay has elapsed In one example, a resistive-capacitive (RC) circuit can be used to effect the desired delay.

In a further aspect, the power harvesting unit can comprise an antenna configured to receive the external energizing magnetic field; a first capacitor coupled to the antenna that is configured to store energy in the resonance mode; and a means for rectifying and at least doubling voltage to be stored in a second capacitor for use by the sensor at a subsequent time.

FIGURES

The accompanying drawings, which are incorporated in and constitute a part of this specification, illustrate certain aspects of the instant invention and together with the description, serve to explain, without limitation, the principles of the invention. Like reference characters used therein indicate like parts throughout the several drawings.

DETAILED DESCRIPTION OF THE DESCRIPTION

The present invention can be understood more readily by reference to the following detailed description, examples, drawing, and claims, and their previous and following description. However, before the present devices, systems, and/or methods are disclosed and described, it is to be understood that this invention is not limited to the specific devices, systems, and/or methods disclosed unless otherwise specified, as such can, of course, vary. It is also to be understood that the terminology used herein is for the purpose of describing particular aspects only and is not intended to be limiting.

The following description of the invention is provided as an enabling teaching of the invention in its best, currently known embodiment. To this end, those skilled in the relevant art will recognize and appreciate that many changes can be made to the various aspects of the invention described herein, while still obtaining the beneficial results of the present invention. It will also be apparent that some of the desired benefits of the present invention can be obtained by selecting some of the features of the present invention without utilizing other features. Accordingly, those who work in the art will recognize that many modifications and adaptations to the present invention are possible and can even be desirable in certain circumstances and are a part of the present invention. Thus, the following description is provided as illustrative of the principles of the present invention and not in limitation thereof.

As used throughout, the singular forms "a," "an" and "the" include plural referents unless the context clearly dictates otherwise. Thus, for example, reference to "a capacitor" can include two or more such capacitors unless the context indicates otherwise.

Ranges can be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint.

As used herein, the terms "optional" or "optionally" mean that the subsequently described event or circumstance may or may not occur, and that the description includes instances where said event or circumstance occurs and instances where it does not.

The present invention comprises wireless physical property sensors incorporating active circuitry and systems incorporating the same. Optionally, the sensors can be integrated with a hermetic, unitary package. Active circuitry comprises, e.g., integrated circuits (ICs). The inclusion of active circuitry in the electrical design of a wireless sensor imparts many new traits. It enables the sensor to sense multiple physical outputs of interest such as, but not limited to, temperature, flow, stress, strain, and chemical properties. The addition of active circuitry also decouples the parasitic effects that would otherwise present signal processing challenges, allows for precise compensation or calibration of the sensor and enables some level of real-time statistical computing, averaging, filtering or combination thereof to ensure the statistical fidelity of the information collected by the sensor. The active circuitry can be used to manage the power source—be it an on-board temporary (e.g., a capacitor or ultra-capacitor) or a permanent (e.g., a battery) source of energy to operate the sensor in a partially or fully autonomous manner. The active circuitry allows for storage of multiple sets of information collected by the sensor or used in processing of the sensor data. Also, the active circuitry enables the storage of personal information relative to the identity of the host and/or the sensor. Furthermore, the active circuitry can enable the use of robust protocols and data transmission techniques to communicate with the interrogator, minimizing the risk of miscommunication and simplifying the interrogator. Sensors ascending to the present invention find widespread use in biomedical, industrial, consumer and automotive applications.

Two distinct types of wireless sensors embodying the characteristics of the prior paragraphs are disclosed herein: analog and digital sensors. The terms "analog" and "digital" refer to the format of communication between the sensor and the interrogator. The analog sensor generates a variable frequency signal whose frequency precisely represents the data to be retrieved. The digital sensor digitizes information collected by the sensor prior to transmitting it to the interrogator using some type of binary modulation such as, without limitation, PSK, ASK and FSK.

Analog Wireless Sensor

In one aspect, the analog wireless sensor is comprised of the following components: a power harvesting unit, an "end of burst" detection unit, a voltage regulation unit, a transducing oscillator unit, and a transmitting coil. Each of these components, as well as their overall assembly and packaging, are exemplarily described below.

The power harvesting unit is comprised of an inductor (L) and a capacitor (C). The inductor couples RF magnetic fields and the capacitor forms a resonant circuit when connected with the inductor and rectifying diodes, energy storage capacitors, and over-voltage protection units. The L and C are tuned to the RF magnetic field present with the following equation for maximum energy harvesting.

$$f = (2*\pi*(LC)^{1/2})^{-1} \quad \text{Equation (1)}$$

The number of rectifying diodes used varies according to the geometry of the circuit. At least one rectifying diode for half wave rectification and a plurality of rectifying diodes for full wave rectification are needed. In one non-limiting example, a minimum of one rectifying diode for half wave rectification and four rectifying diodes for full wave rectification can be used. Optionally, when higher voltage generation is required, a voltage multiplying scheme can be employed, such implementation can involve the addition of a number of diodes and capacitors. The energy storage capacitor employs relatively large capacitance value compared to other capacitors in the circuit because it is the only energy source for operation of the wireless sensor in sequential systems. The value can vary from hundreds of pico Farad to tens of microFarad. A Zener diode can be used as an over-voltage protection unit.

Figure 1:
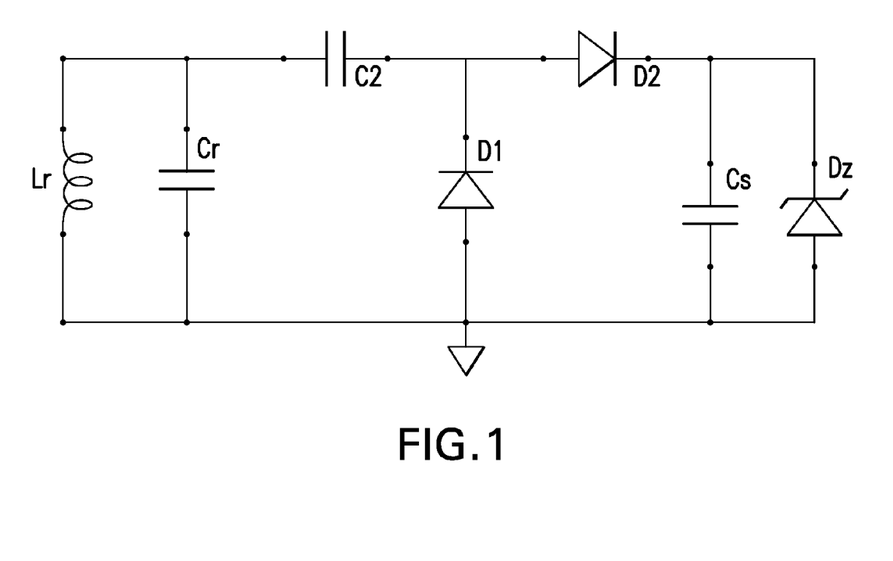
FIG. 1 is a schematic circuit diagram showing one embodiment of a power harvesting unit that employs a voltage doubling scheme.

FIG. 1 shows one embodiment of a power harvesting unit that employs a voltage doubling scheme. When the interrogator an generates energizing magnetic field in proximity to the sensor, the small antenna (Lr) and a capacitor (Cr) pick up the AC voltage in resonance mode. That AC voltage is rectified and charged to a first capacitor C2 through diode D1. Again, the voltage charged in C2 is added to the AC voltage in Lr and Cr, and rectified and charged to capacitor Cs through diode D2. Now due to C2, D1, and D2, the AC voltage available in Lr and Cr is doubled and stored to a second capacitor, Cs, as a DC voltage to be used for sensor operation at a subsequent time. A zener diode (Dz) may be incorporated to provide over-voltage protection. This circuit is useful, when the sensor chip used requires high voltage.

In one aspect, in order to recognize the end of the RF magnetic burst around the sensor, a simple resistive-capacitive (RC) circuit can be used. The capacitor of the RC circuit remains charged while RF field is present. As soon as RF field is removed, the capacitor of the RC circuit discharges through the resistor of the RC circuit with a predetermined time delay. In one aspect, the time delay is programmed such that energizing RF magnetic field has decayed to a given threshold level. When the RC circuit has discharged, the rest of the circuit "wakes up" for data transmission—i.e., the discharge of the capacitor triggers a switch to connect the rest of the circuit to the energy storage capacitor. Thus, the potential problem of interference of the RF field is avoided and the sensor is able to take advantage of the maximum time available for communication.

Figure 2:
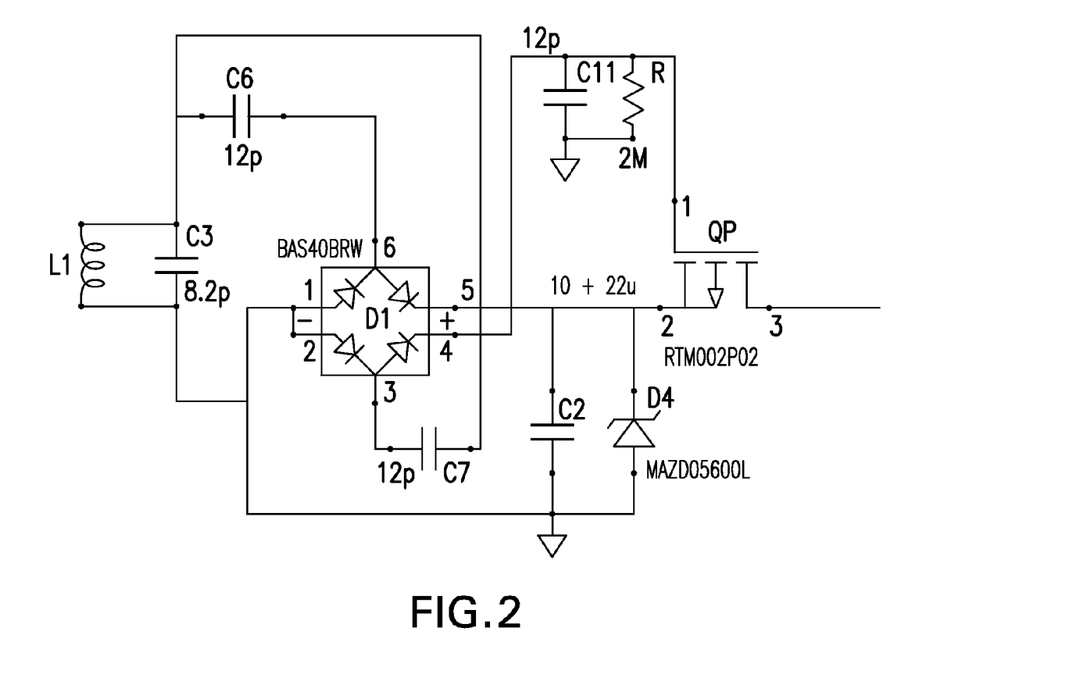
FIG. 2 is a schematic circuit diagram showing one embodiment of a circuit comprising a power harvesting unit and an end of burst detection unit.

FIG. 2 depicts one embodiment of a circuit comprising a power harvesting unit and an end of burst detection unit. When the interrogator generates an energizing magnetic field in proximity to the sensor, the electrical energy (i.e., voltage) is harvested and stored to capacitor C2. During this energy harvesting time, transistor switch QP is open, so that the energy being stored is not available to the main sensor circuit and is thus preserved. The main sensor circuit will be connected to the #3 node of switch QP later. As soon as the energizing magnetic field disappears, switch QP closes (the #2 and #3 nodes of QP are electrically connected), and the voltage in C2 is available to power the sensor.

The detailed explanation of the circuit depicted in FIG. 2 is as follows: the L1 and C3 pick up the AC voltage which is doubled and rectified to C2 through C6 and two diodes in BAS4OBRW (#1 and #5 node in BAS4OBRW). Simultaneously, the AC voltage in L1 and C3 is doubled and rectified to C11 through C7 and two diodes in BAS4OBRW (#2 and #4 node in BAS4OBRW). Due to the voltage in C11, the switch QP is open and the energy in C3 is not available to the #3 node of switch QP. When the energizing field from the interrogator is off, the voltage in C11 dissipates through resistor R and becomes zero in short time (i.e., less than a millisecond). As soon as the voltage in C11 becomes zero, the switch QP closes and the voltage in C2 is available to main sensor circuit.

Thus, in one exemplary embodiment, the power harvesting unit is a LC-tank that is followed by a rectification stage and an optional voltage multiplication stage. It is then an energy storage stage, such as a capacitor with a desired energy storage space.

Most of electronic oscillators call for precise control of supply voltage for accurate operation. This is true for the RC oscillator used in this scheme. Because the voltage source in the analog wireless sensor is a capacitor, the supply voltages decay unless the capacitance value is impractically large. A linear voltage regulator and a voltage reference can be used for its preciseness and simplicity. Since the linear voltage regulator and the voltage reference do not control voltage below their rated voltage, an under-voltage lockout is employed to avoid uncontrolled operation under the rated voltage of the linear voltage regulator and voltage reference by turning off the subsequent circuit when the voltage drops below the predetermined value.

Figure 3:
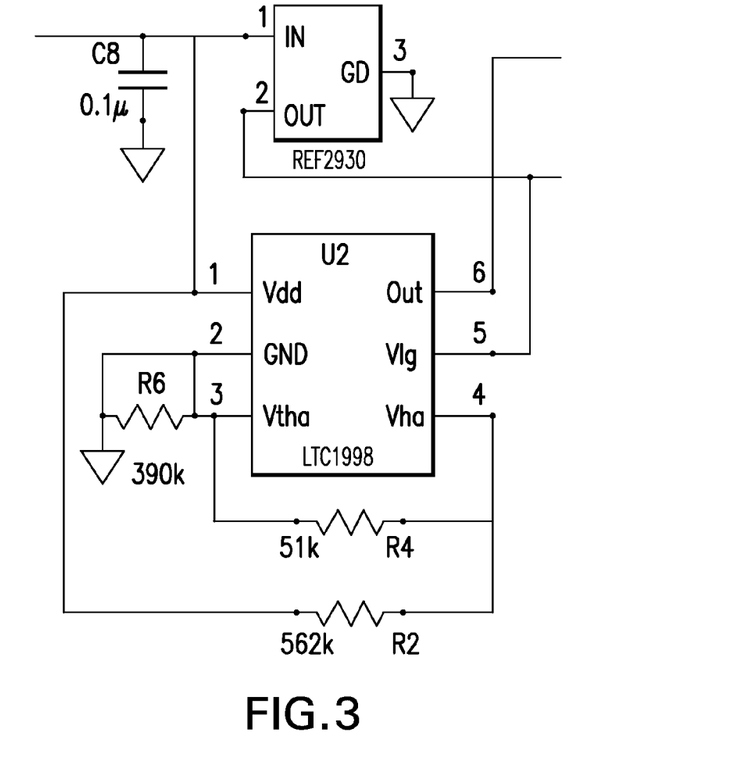
FIG. 3 is a schematic circuit diagram illustrating one embodiment of a circuit having a voltage regulation circuit.

FIG. 3 illustrates one embodiment of a circuit having a voltage regulation circuit. The unit V1 is a voltage reference and U2 is an under-voltage lockout unit. C8 is noise reduction capacitor. The #1 node of V1 is connected to #3 node of QP switch, therefore the voltage stored in C2 is available to the #1 node of V1. VI functions to output a preset voltage level whenever the input (#1) voltage is higher than preset output voltage. This ensures the voltage available to sensor transducer unit is substantially constant The sensor transducer unit is connected to output (#2) of V1. The constant level of voltage contributes to the accurate functioning of the transducer unit. However, if the input voltage (#1 node) of V1 is lower than preset output voltage (#2 node), the output voltage of V1 follows the input regardless of the preset output. This voltage variation can add noise to sensor transducer function when it is supplied to transducer unit. In order to manage this low-voltage faulty condition, U2 is employed. U2 monitors voltage in C8 and, if the voltage in C8 is smaller than preset voltage, it generates a warning or disabling signal through #6 node of U2. The preset voltage level is adjusted with resistor values in R2, R4, and R6. When the voltage is higher than the preset voltage, then the preset voltage is available to #6 node of U2. When the voltage in C8 is lower than the preset voltage, the zero voltage is available to #6 node of U2, either warning or disabling transducer unit.

Next, the transducing oscillator unit converts physical properties such as, but not limited to, pressure, temperature, stress and the like to electrical signals. Subsequently, the electrical signals set the electrical oscillation frequency, which is transmitted to the interrogator. This electrical frequency can be measured and correlated to the value of the measured physical property by the interrogator.

The RC time constant-based oscillator can be used for setting the electrical oscillation frequency. One example is a 555 timer. In one aspect, the relationship between frequency and the sensed property is described with the equation below:

$$f = (kRC)^{-1}, \quad \text{Equation (2)}$$

where k is a proportional constant varying by design and operation frequency, R and C are, respectively, the resistor and capacitor values that sense the physical property of interest. It is contemplated that either one of the R or C values can be held constant and the other can be used to sense the physical property of interest.

Figure 4:
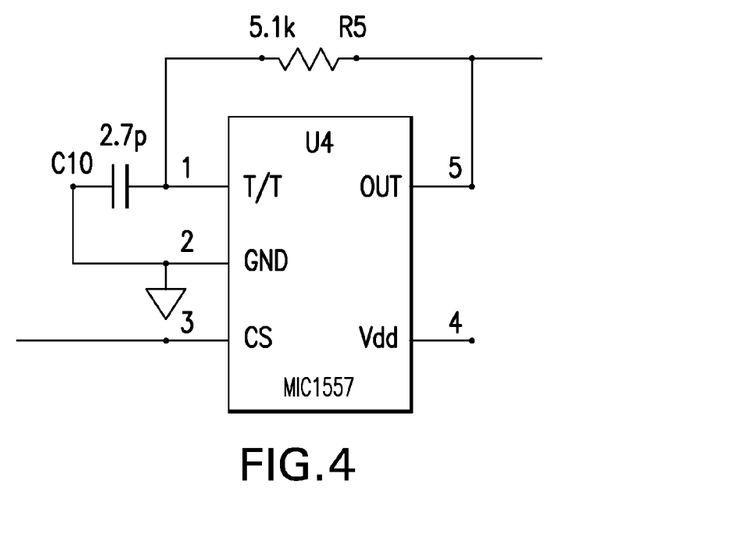
FIG. 4 is a schematic circuit diagram showing one embodiment of a circuit schematic for the RC time-based oscillator unit.

FIG. 4 shows one embodiment of a circuit schematic for the RC time-based oscillator unit. In this exemplary aspect, a capacitor (C10) or a resistor (R5) represents the sensing capacitor or sensing resistor. The #4 node is an operating-voltage supply line, and #3 node is a chip-function enabling line. In this aspect, if zero voltage is supplied to #3 node, the whole chip is configured to shut down. In a further aspect, the line that is in communication with the #3 node can also be electrically coupled to the #6 node of U2 in the FIG. 3, which acts to shut down the chip when the voltage is lower than the preset voltage. In one aspect, the exemplary circuit is configured such that the oscillator frequency can be varied by the value of C10 and R5 and can be available through the #5 node in order to be transmitted back to the reader or interrogator wirelessly.

Conventionally, a passive (no battery) LC resonant circuit is composed of two electrical passive components that are connected in series: a coil or inductor ("L"), and a capacitor ("C"). Such a passive electrical circuit exhibits electrical resonance when subjected to an alternating electromagnetic field. In one aspect, the electrical resonance is particularly acute for a specific frequency value or range of the impinging signal. When the impinging signal substantially reaches the resonant frequency of the LC resonant circuit inside the sensor assembly, a pronounced disturbance of the field can be detected wirelessly. In the simplest approximation, the electrical resonance occurs for a frequency f, related to the value of L and C according to equation 1 above.

The passive electrical resonant circuit for the assemblies described herein that utilize a passive electrical resonant circuit can be fabricated via conventional MEMS approach to sensor design, which lends itself to the fabrication of small sensors that can be formed using biocompatible polymers as substrate materials. In a further aspect, appropriately biocompatible coatings can be applied to the surfaces of the respective assemblies in order to prevent adhesion of biological substances to the respective assemblies that could interfere with their proper function.

In one example, it is contemplated that the passive electrical resonant circuit of the assembly can be manufactured using Micro-machining techniques that were developed for the integrated circuit industry. An example of this type of sensor features an inductive-capacitive (LC) resonant circuit with a variable capacitor is described in Allen et al., U.S. Pat. No. 6,111,520, which is incorporated herein by reference. In this sensor, the capacitance varies with the pressure of the environment in which the capacitor is placed. Consequently, the resonant frequency of the exemplary LC circuit of the Allen pressure sensor varies depending on the pressure of the environment.

In one aspect, to convert stress to resistance, piezoresistive material can be used to transduce sensed stress to resistance. An example of this type of sensor is exemplarily described in Gershenfeld et al., U.S. Pat. No. 6,025,725, which is incorporated herein by reference.

In one aspect, to convert temperature to resistance, a thermistor can be employed. In this aspect, the thermistor is defined as a metal whose specific electrical resistance varies according to the temperature of a material. The environmental temperature determines the resistance which, in turn, determines the oscillation frequency of the RC oscillator unit. In this aspect, the thermistor is attached to the sensor housing for better thermal conduction.

Thus, it is contemplated that the sensor can be configured to convert a sensed physical property into an electrical signal comprises. For example and without limitation, this conversion can comprise converting sensed temperature changes to resistance changes via a temperature sensitive resistor. Further, for example and without limitation, this conversion can comprise converting sensed changes in pressure to changes in capacitance values via a pressure sensitive capacitor. In another example, for example and without limitation, this conversion can comprise converting sensed stress changes to resistance changes via a stress sensitive resistor.

Optionally, a voltage controlled oscillator (VCO) can also be used for transducing a physical property of interest to an electrical signal. A conventional VCO is an electronic circuit whose electrical oscillation output is a function of the voltage applied. In this aspect, the measured physical property is converted to a voltage that determines the broadcasting electrical frequency. Many physical properties are readily converted to voltage. For example, and without limitation, such convertible physical properties include measured temperature, stress, pressure or the like.

In one exemplary aspect, to accomplish a temperature to voltage transduction, a constant current source can be applied to a resistor. Here, the induced voltage at the end of the resistor is proportional to the value of the resistor. Therefore, temperature change can be converted to voltage through a thermistor.

In an additional exemplary aspect, to accomplish a stress or pressure to voltage transduction, four piezoresitors can be arranged into a Wheatstone bridge configuration, which is configured to achieve a higher voltage sensitivity while geometrically compensating for temperature effects. In this aspect, the stress applied by the external environment to the deformable region of the sensor determines the output voltage of the Wheatstone bridge, and which sets the electrical oscillation for broadcasting.

Optionally, it is contemplated that an identification signal or signature can be added to the transmitted signal. In order to attach such a signature, the oscillation frequency can be amplitude modulated prior to transmission to the interrogator. Subsequently, the interrogator can confirm this signature and authenticate that the frequency is coming from a specific wireless sensor or merely the wireless sensor at all. This signature modality allows for sensor identification and avoids any confusion with other resonances present in the environment.

Digital Wireless Sensor

In one aspect, a digital wireless sensor is comprised of the following components: a power harvesting unit, an end of burst detection unit, a microcontroller unit (MCU), a transducing analog-to-digital converter unit, and a transmitting coil. Optionally, a voltage regulation unit can be incorporated into the digital wireless sensor. The design of the power harvesting unit, the end of burst detection unit and the voltage regulation unit are substantially the same for the digital sensor as described above for the analog sensor.

Figure 5:
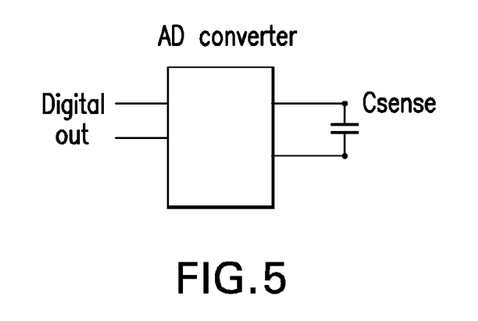
FIG. 5 is a schematic circuit diagram showing a variable capacitor and an IC that is configured to convert capacitance to a digital signal are utilized to form a digital sensor with a transducing capacitor.
Figure 6:
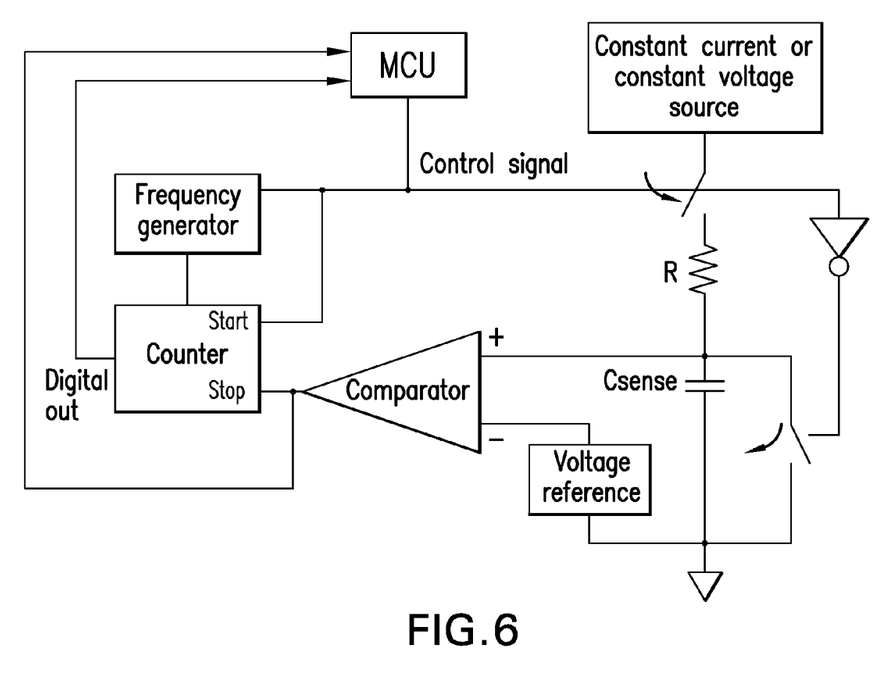
FIG. 6 is a schematic circuit diagram showing an MCU controlling the timing of the rest of the circuit. In addition, the MCU can provide the control signal for the transducing A-to-D converting unit, can store the measured data into local memory, and can deliver modulated data for transmission to the interrogator.

As shown in FIG. 5, a variable capacitor and an IC that is configured to convert capacitance to a digital signal are utilized to form a digital sensor with a transducing capacitor. In operation, as indicated in FIG. 6, the MCU sends out a signal to start the frequency generator and the counter. Substantially simultaneously, the capacitance is charged at a controlled rate. In one non-limiting example, a constant current source or a constant voltage source can be used to charge the capacitor. One skilled in the art will appreciate that the constant current source does not require a resistor can also produce a more linear digital output over a wide range of capacitance.

When the voltage of the capacitor reaches the reference voltage of the voltage regulator, the comparator trips and the counter is turned off. The MCU reads the digital output and discharges the capacitor in preparation for the next measurement. In one aspect, the digital output is a number that is substantially proportional to the capacitance value. In a further aspect, the digital output resolution depends on the frequency of the frequency generator, which should be kept high enough to support resolution of the capacitance value necessary for meaningful output to the end user of the system.

As schematically shown in FIG. 6, the MCU controls the timing of the rest of the circuit. In addition, the MCU can provide the control signal for the transducing A-to-D converting unit, can store the measured data into local memory, and can deliver modulated data for transmission to the interrogator. Conventional off-the-shelf MCU chips typically comprise a frequency generator, a counter, and a comparator with voltage references, and can realize the schematic in FIG. 6 with minimal components added.

Figure 8:
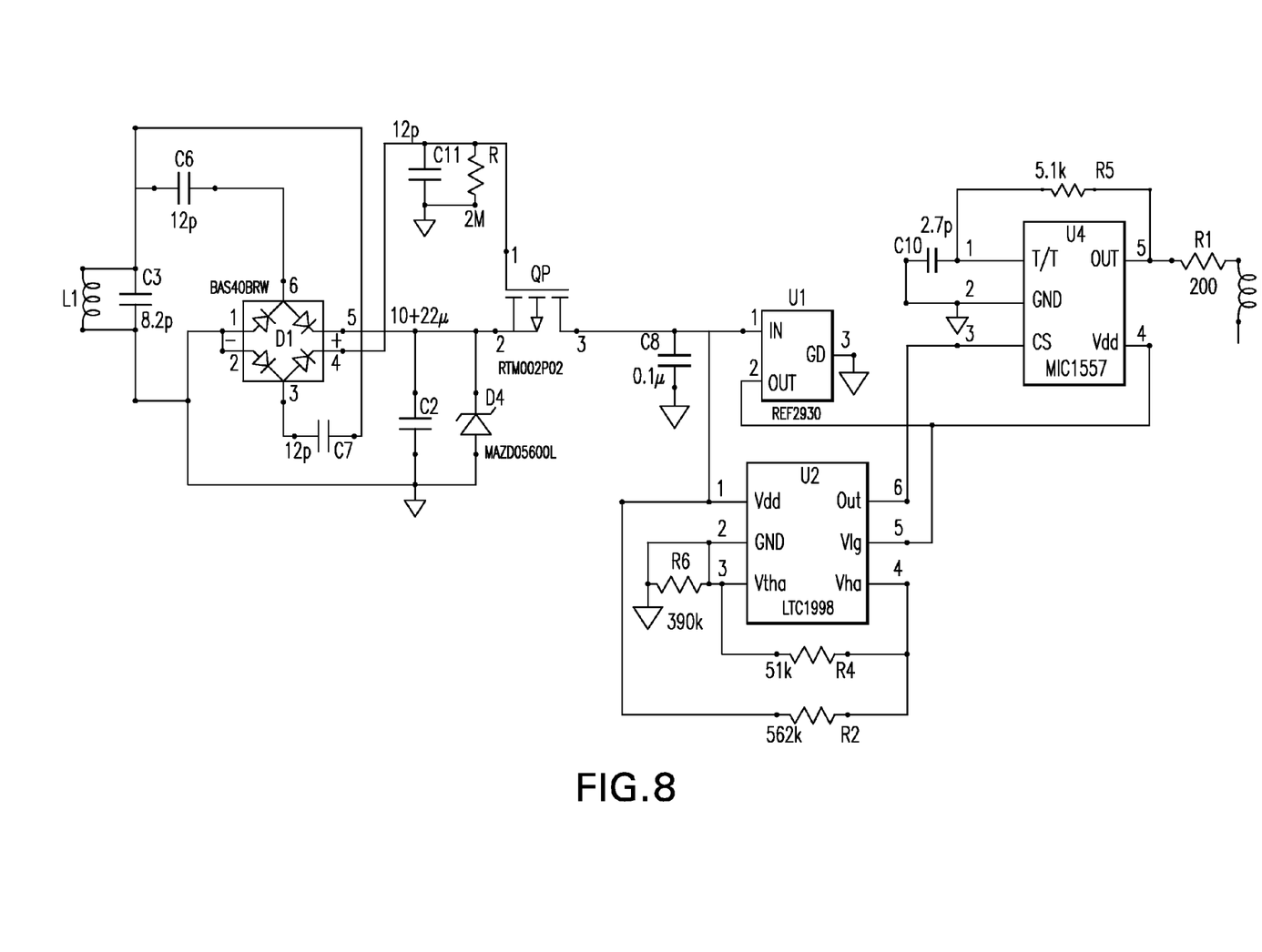
FIG. 8 is a schematic circuit diagram of an exemplary embodiment of a wireless sensor showing a coil (L1) that is an energy harvesting coil and a capacitor (C10) or a resistor (R5) that varies predictably with the measured physical property. In one aspect, a coil (L2) serves as a transmitting coil and a resistor (R1) acts as an attenuator.

FIG. 8 shows a schematic circuit diagram of an exemplary embodiment of a wireless sensor. As mentioned previously, a coil (L1) is an energy harvesting coil and a capacitor (C10) or a resistor (R5) varies predictably with the measured physical property. In one aspect a coil (L2) serves as a transmitting coil and a resistor (R1) acts as an attenuator.

Figure 9:
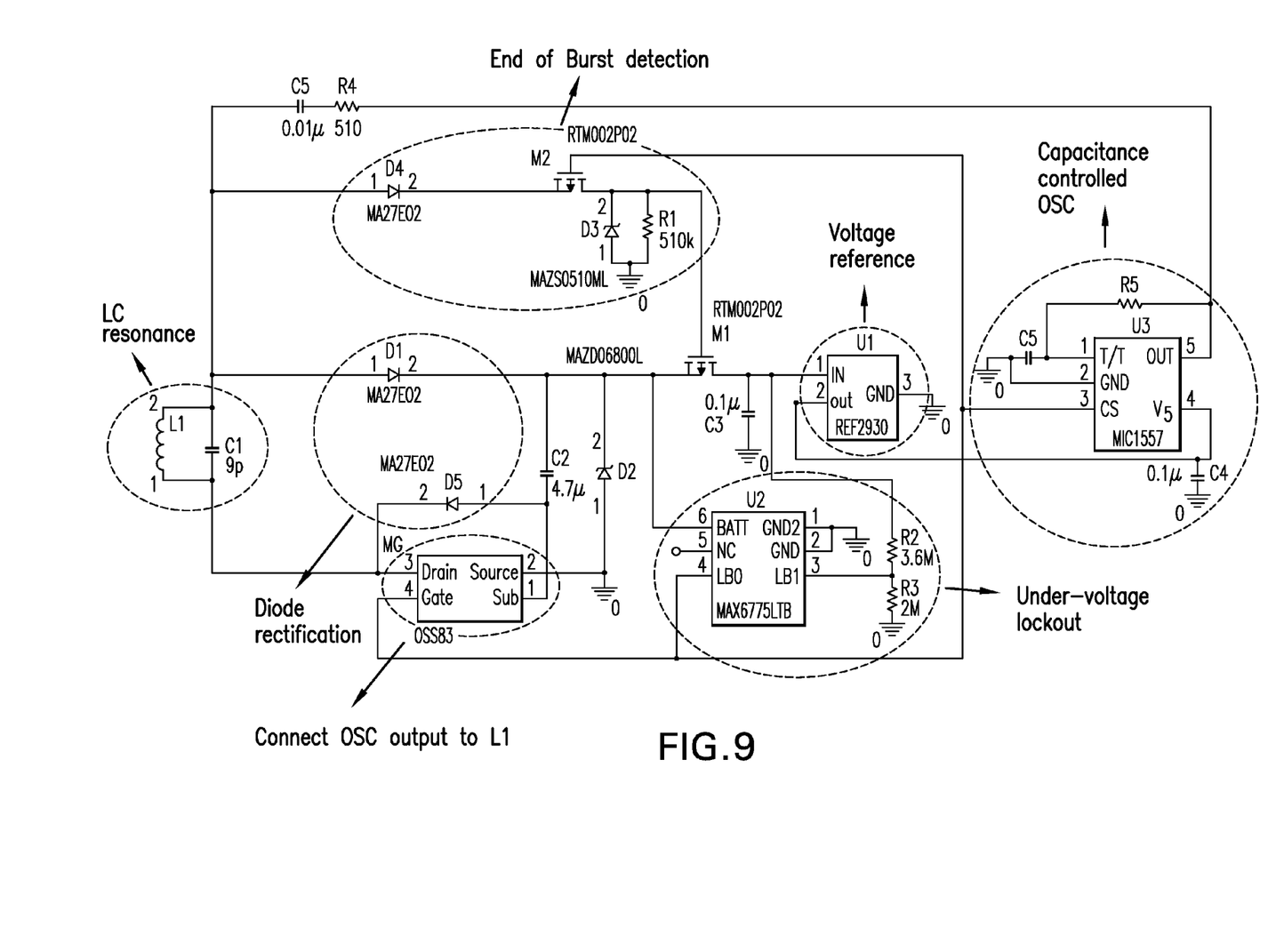
FIG. 9 depicts a schematic circuit diagram for an exemplary embodiment of a wireless sensor that uses one coil instead of two.
Figure 10:
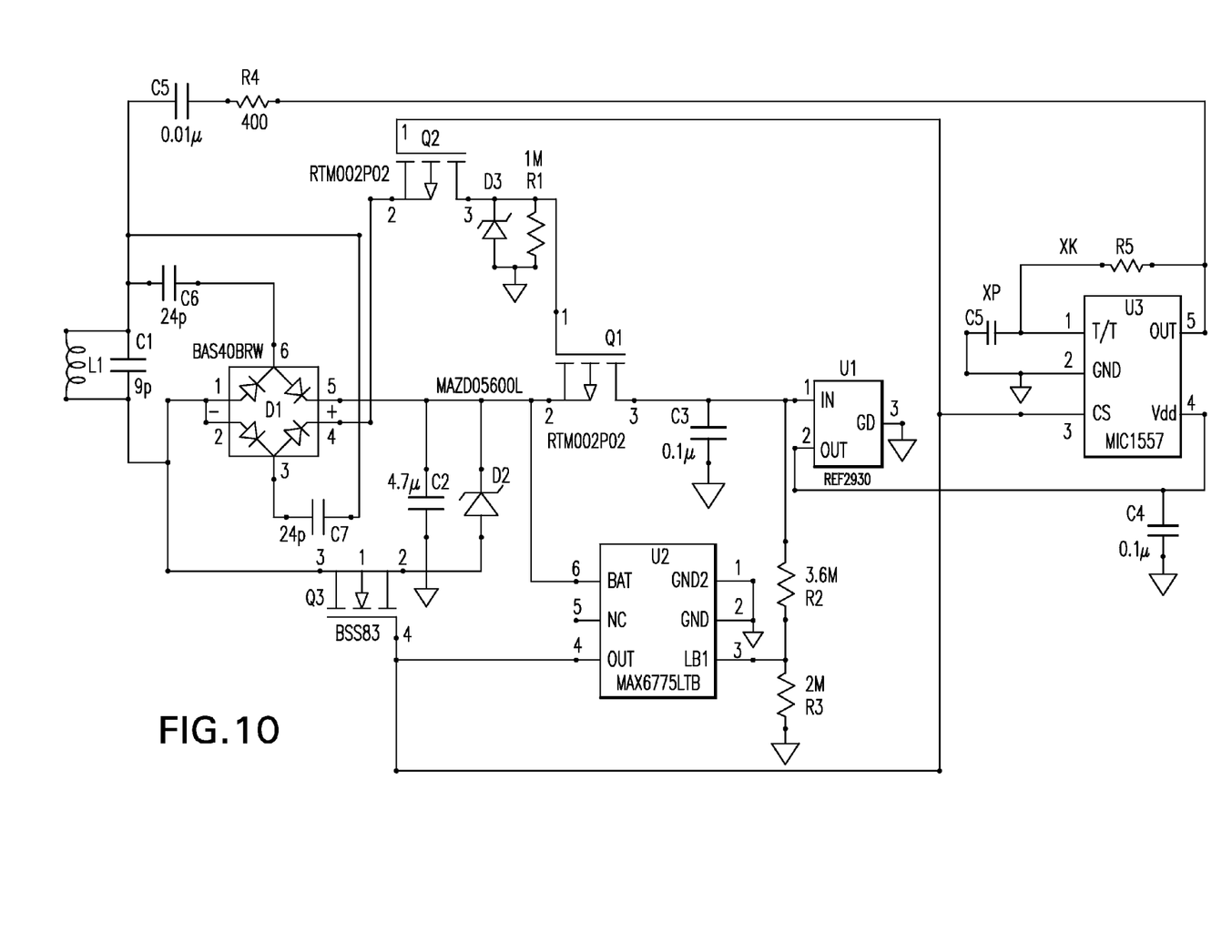
FIG. 10 depicts the same exemplary circuit as in FIG. 9 but with a voltage doubling scheme.

FIG. 9 depicts a schematic for an exemplary embodiment of a wireless sensor that uses one coil instead of two. In one aspect the plurality of inductor coils employed in the previous examples are not functionally active simultaneously, i.e., the transmit coil is not in use while the energy pick up coil is active and vice-versa. Therefore, a single coil wireless sensor is achievable with certain modifications. In this aspect, the output of the transducer oscillator can be connected to the coil (L1) through MOSFET switch M3 whenever the transducer oscillator activates and transmits a signal. Thus, coil L1 can be used for both energy harvesting and signal transmission. FIG. 10 depicts the same circuit as in FIG. 9 but with a voltage doubling scheme.

Packaging of Wireless Sensors

Figure 7A:
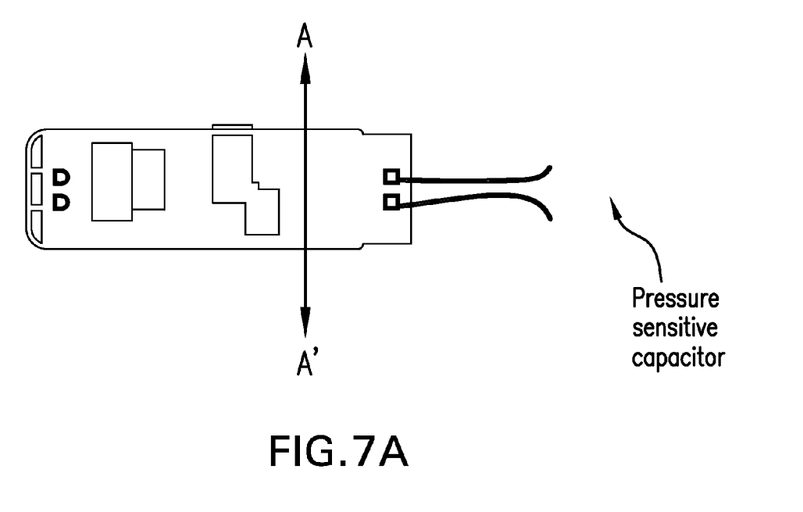
FIGS. 7(a) and 7(b) illustrate one embodiment of a PCB-based sensor circuit encapsulated by a fused silica housing.
Figure 7B:
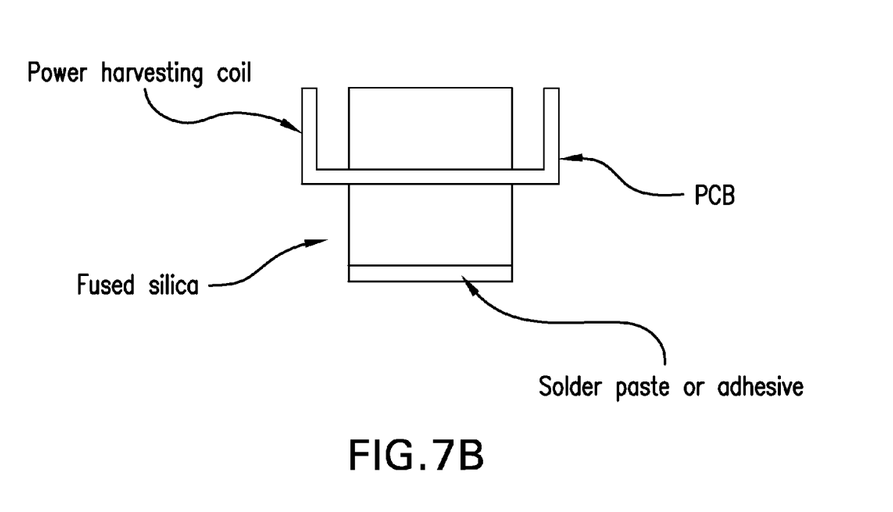

In one aspect, the packaging of the sensors can comprise encapsulating PCB-based sensor circuits in ceramic housings. For example and without limitation, the ceramic housing can be completed either via laser fusion, anodic bonding or eutectic bonding. It is of course contemplated that the PCB-based sensor circuit can be replaced with an ASIC and this replacement is within the scope of the present invention. In various exemplary aspect, the sensor can be packaged by the methods disclosed in U.S. patent application Ser. No. 11/472,905, filed Jun. 22, 2006; U.S. patent application Ser. No. 11/314,046, filed Dec. 20, 2005; U.S. patent application Ser. No. 11/157,375, filed Jun. 21, 2005; all of which are incorporated herein by reference in their entireties. In one aspect, FIGS. 7(a) and 7(b) illustrate one possible embodiment of a PCB-based sensor circuit encapsulated by a fused silica housing.

In one aspect, in operation, it is contemplated that the external source of the energizing magnetic field, such as an interrogator, will transmit energy at a substantially constant preselected frequency. In a further aspect, the external source will activate or energize for a predetermined period of time, during which time the power harvesting unit of the wireless sensor is energized. After the predetermined period of energizing time has passed, energy accumulated in the power harvesting unit is supplied to the voltage regulation unit and is subsequently supplied to the transducing oscillator unit at the substantially constant preset voltage level output from the voltage regulation unit. Subsequently, the electrical signal indicative of the sensed physical property is transmitted via the transmitting coil of the sensor to a remote, external antenna, which can form a portion of the interrogator.

EXPERIMENTAL

Figure 11:
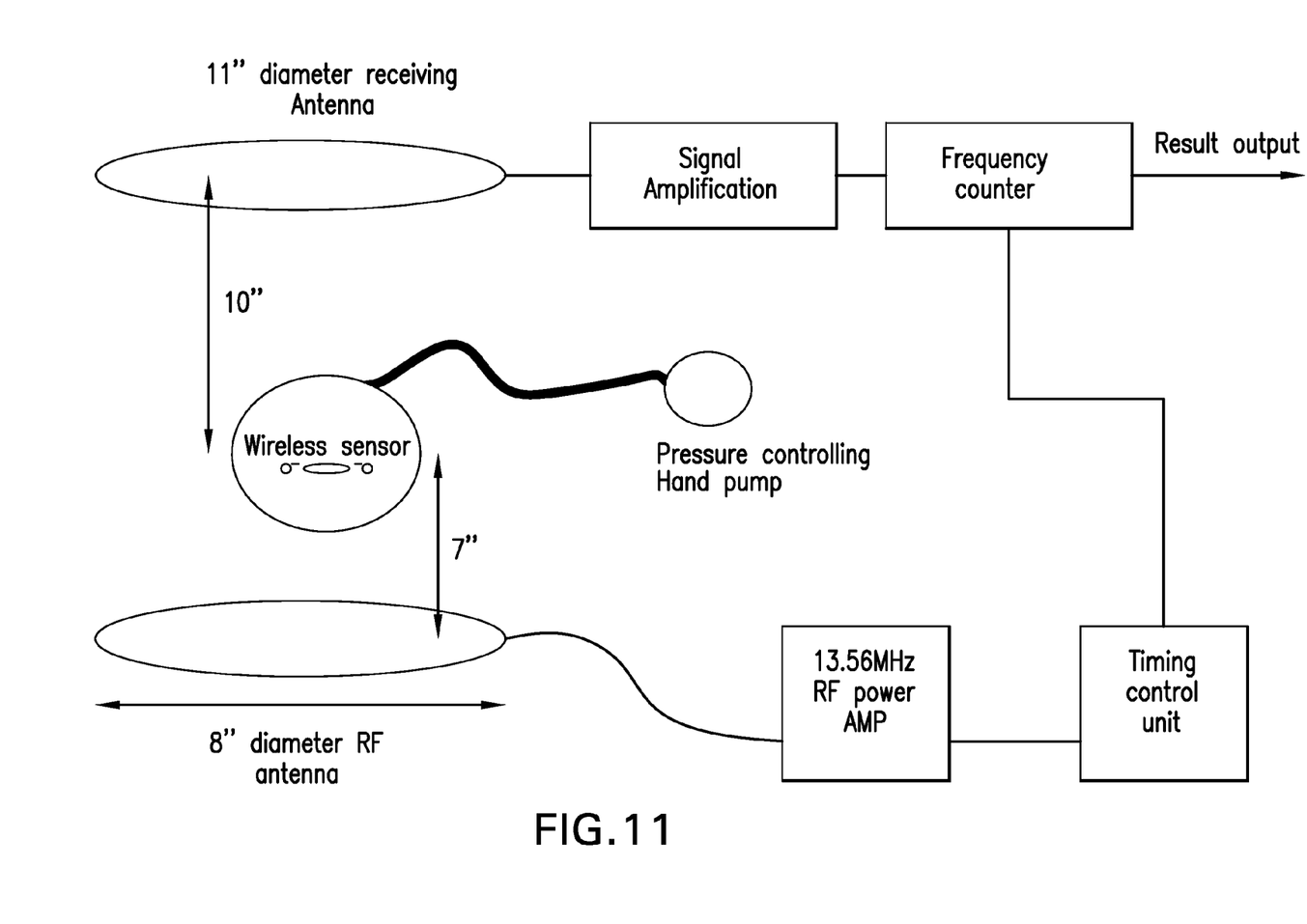
FIG. 11 is a schematic illustration of an exemplary experimental set-up used in one pressure sensing experiment.

FIG. 11 shows the brief illustration of an exemplary experimental set-up used in one pressure sensing experiment. In this experiment, the capacitor (C 10) in the schematic illustrated in FIG. 8 is replaced with a pressure sensitive capacitor. Pressure was applied to the sensor via a hand pump.

Figure 12:
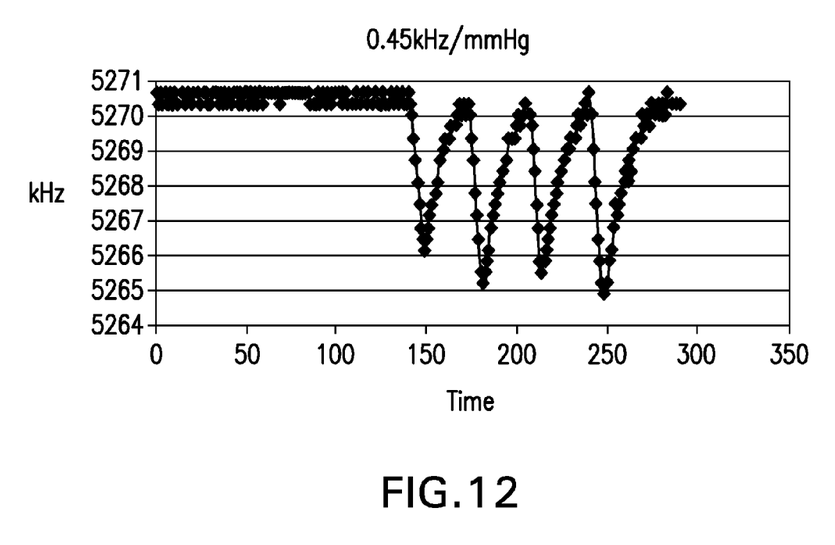
FIG. 12 is a graph showing the results of the pressure sensing experiment schematically shown in FIG. 11.

In this experiment, the timing control unit sent out periodic triggering (on/off) signal to RF power amp. A strong 13.56 MHz signal was turned on/off at a rate of 35 Hz and subsequently feed to the antenna. Here, whenever the 13.56 MHz signal is turned off, the wireless pressure sensor "wakes up" and transmits the pressure information in the form of electrical frequency. A receiving antenna sensed the transmitted frequency by wireless sensor, and then the received signal was amplified and feed to the frequency counter. The results of the experiment are shown in FIG. 12.

These and other modifications and variations to the present disclosure can be practiced by those of ordinary skill in the art, without departing from the spirit and scope of the present disclosure, which is more particularly set forth in the appended claims. In addition, it should be understood that aspects of the various embodiments can be interchanged both in whole or in part. Furthermore, those of ordinary skill in the art will appreciate that the foregoing description is by way of example only and is not intended to limit the disclosure so further described in such appended claims.

What is claimed is:

1. An implantable wireless sensor, comprising:
   a power harvesting unit comprising:
     an antenna configured to receive an external energizing magnetic field;
     a first capacitor coupled to the antenna configured to resonate at a predetermined frequency; and
     a means for rectifying voltage to be stored in a second capacitor for use by the sensor at a subsequent time;
   a voltage regulation unit electrically coupled to the power harvesting unit, wherein the voltage regulation unit is configured to actuate at a minimum voltage level;
   a transducing oscillator unit electrically coupled to voltage regulation unit, wherein the transducing oscillator unit comprises a means for converting a sensed physical property into an electrical signal; and
   a transmitting coil configured to receive the electrical signal and to transmit the electrical signal to an external antenna;
   wherein the sensed physical property is selected from a group consisting of: pressure, stress, strain, or temperature.

2. The implantable wireless sensor of claim 1, further comprising a means for delaying energizing the voltage regulation unit until a predetermined time delay has elapsed.

3. The implantable wireless sensor of claim 2, wherein the means for delaying energizing the voltage regulation unit until a predetermined time delay has elapsed is coupled to the power harvesting unit and the voltage regulation unit.

4. The implantable wireless sensor of claim 3, wherein the means for delaying energizing the voltage regulation unit until a predetermined time delay has elapsed comprises a resistive-capacitive (RC) circuit.

5. The implantable wireless sensor of claim 4, wherein the RC circuit is configured to activate a solid state switch connected between the power harvesting unit and the voltage regulation unit.

6. The implantable wireless sensor of claim 4, wherein the RC circuit comprises a capacitor coupled to a resistor, wherein the capacitor is configured to store energy during the application of an external energizing magnetic field and wherein the stored energy is discharged through the resistor over the predetermined time delay upon removal of the external energizing magnetic field.

7. The implantable wireless sensor of claim 1, wherein the means for rectifying voltage to be stored in the second capacitor further comprises at least doubling the voltage to be stored in the second capacitor.

8. The implantable wireless sensor of claim 7, wherein the power harvesting unit further comprises a zener diode operable coupled to the second capacitor.

9. The implantable wireless sensor of claim 1, wherein the voltage regulation unit comprises:
   a voltage reference unit electrically coupled to the power harvesting unit, wherein the voltage reference unit is configured to output a substantially constant preset voltage level when the received voltage from the power harvesting unit is higher than the preset output voltage; and
   an under-voltage lockout unit that is electrically coupled to the voltage reference unit.

10. The implantable wireless sensor of claim 1, wherein the means for converting a sensed physical property into an electrical signal comprises a means for converting sensed temperature changes to resistance changes.

11. The implantable wireless sensor of claim 10, wherein the means for converting sensed temperature changes to resistance changes comprises a temperature sensitive resistor.

12. The implantable wireless sensor of claim 1, wherein the means for converting a sensed physical property into an electrical signal comprises means for converting sensed changes in pressure to changes in capacitance values.

13. The implantable wireless sensor of claim 12, wherein the means for converting sensed changes in pressure to changes in capacitance values comprises a pressure sensitive capacitor.

14. The implantable wireless sensor of claim 1, wherein the means for converting a sensed physical property into an electrical signal comprises means for converting sensed stress changes to resistance changes.

15. The implantable wireless sensor of claim 14, wherein the means for converting sensed stress changes to resistance changes comprises a stress sensitive resistor.

16. The implantable wireless sensor of claim 1, wherein the means for converting a sensed physical property into an electrical signal comprises a voltage controlled oscillator.

17. The implantable wireless sensor of claim 16, wherein the voltage controlled oscillator comprises a means for converting the sensed physical property to a voltage that determines the frequency of the output of the voltage controlled oscillator.

18. The implantable wireless sensor of claim 1, wherein the electrical signal further comprises an identification signal that is unique to each sensor.

19. The implantable wireless sensor of claim 1, wherein the power harvesting unit is a LC-tank.

20. An implantable wireless sensor, comprising:
   a power harvesting unit comprising:
     an antenna configured to receive an external energizing magnetic field;
     a first capacitor coupled to the antenna configured to resonate at a predetermined frequency; and
     a means for rectifying voltage to be stored in a second capacitor for use by the sensor at a subsequent time;
   a voltage regulation unit electrically coupled to the power harvesting unit, wherein the voltage regulation unit is configured to actuate at a minimum voltage level;
   a means for delaying energizing the voltage regulation unit until a predetermined time delay has elapsed;
   a transducing oscillator unit electrically coupled to voltage regulation unit, wherein the transducing oscillator unit comprises a means for converting a sensed physical property into an electrical signal; and a transmitting coil configured to receive the electrical signal and to transmit the electrical signal to an external antenna;

wherein the sensed physical property is selected from a group consisting of: pressure, stress, strain, or temperature.

21. The implantable wireless sensor of claim 20, wherein the means for delaying energizing the voltage regulation unit until a predetermined time delay has elapsed is coupled to the power harvesting unit and the voltage regulation unit.

22. The implantable wireless sensor of claim 21, wherein the means for delaying energizing the voltage regulation unit until a predetermined time delay has elapsed comprises a resistive-capacitive (RC) circuit.

23. The implantable wireless sensor of claim 22, wherein the RC circuit is configured to activate a solid state switch connected between the power harvesting unit and the voltage regulation unit.

24. The implantable wireless sensor of claim 22, wherein the RC circuit comprises a capacitor coupled to a resistor, wherein the capacitor is configured to store energy during the application of an external energizing magnetic field and wherein the stored energy is discharged through the resistor over the predetermined time delay upon removal of the external energizing magnetic field.

25. The implantable wireless sensor of claim 21, wherein the means for rectifying voltage to be stored in the second capacitor further comprises at least doubling the voltage to be stored in the second capacitor.

26. The implantable wireless sensor of claim 25, wherein the power harvesting unit further comprises a zener diode operable coupled to the second capacitor.

27. The implantable wireless sensor of claim 20, wherein the voltage regulation unit comprises:
a voltage reference unit electrically coupled to the power harvesting unit, wherein the voltage reference unit is configured to output a substantially constant preset voltage level when the received voltage from the power harvesting unit is higher than the preset output voltage; and
an under-voltage lockout unit that is electrically coupled to the voltage reference unit.

28. The implantable wireless sensor of claim 20, wherein the means for converting a sensed physical property into an electrical signal comprises a temperature sensitive resistor.

29. The implantable wireless sensor of claim 21, wherein the means for rectifying voltage to be stored in the second capacitor further comprises at least doubling the voltage to be stored in the second capacitor.

30. The implantable wireless sensor of claim 20, wherein the means for converting a sensed physical property into an electrical signal comprises a stress sensitive resistor.

31. The implantable wireless sensor of claim 20, wherein the means for converting a sensed physical property into an electrical signal comprises a voltage controlled oscillator.

32. The implantable wireless sensor of claim 31, wherein the voltage controlled oscillator comprises a means for converting the sensed physical property to a voltage that determines the frequency of the output of the voltage controlled oscillator.

33. The implantable wireless sensor of claim 20, wherein the electrical signal further comprises an identification signal that is unique to each sensor.

34. The implantable wireless sensor of claim 20, wherein the power harvesting unit is a LC-tank.

35. An implantable wireless sensor, comprising:
a power harvesting unit;
a voltage regulation unit electrically coupled to the power harvesting unit, wherein the voltage regulation unit is configured to actuate at a minimum voltage level;
a means for delaying energizing the voltage regulation unit until a predetermined time delay has elapsed;
a transducing oscillator unit electrically coupled to voltage regulation unit, wherein the transducing oscillator unit comprises a means for converting a sensed physical property into an electrical signal; and
a transmitting coil configured to receive the electrical signal and to transmit the electrical signal to an external antenna;
wherein the sensed physical property is selected from a group consisting of: pressure, stress, strain, or temperature.

36. An implantable wireless sensor, comprising:
a power harvesting unit;
a voltage regulation unit electrically coupled to the power harvesting unit, wherein the voltage regulation unit is configured to actuate at a minimum voltage level and wherein the voltage regulation unit comprises:
a voltage reference unit electrically coupled to the power harvesting unit, wherein the voltage reference unit is configured to output a substantially constant preset voltage level when the received voltage from the power harvesting unit is higher than the preset output voltage; and
an under-voltage lockout unit that is electrically coupled to the voltage reference unit;
a transducing oscillator unit electrically coupled to voltage regulation unit, wherein the transducing oscillator unit comprises a means for converting a sensed physical property into an electrical signal; and
a transmitting coil configured to receive the electrical signal and to transmit the electrical signal to an external antenna;
wherein the sensed physical property is selected from a group consisting of: pressure, stress, strain, or temperature.

37. An implantable wireless sensor, comprising:
a power harvesting unit;
a voltage regulation unit electrically coupled to the power harvesting unit, wherein the voltage regulation unit is configured to actuate at a minimum voltage level;
a transducing oscillator unit electrically coupled to voltage regulation unit, wherein the transducing oscillator unit comprises a means for converting a sensed physical property into an electrical signal; and
a transmitting coil configured to receive the electrical signal and to transmit the electrical signal to an external antenna;
wherein the sensed physical property is pressure, and wherein the means for converting a sensed physical property into an electrical signal comprises means for converting sensed changes in pressure to changes in capacitance.

38. An implantable wireless sensor, comprising:
a power harvesting unit;
a voltage regulation unit electrically coupled to the power harvesting unit, wherein the voltage regulation unit is configured to actuate at a minimum voltage level;
a transducing oscillator unit electrically coupled to voltage regulation unit, wherein the transducing oscillator unit comprises a means for converting a sensed physical property into an electrical signal; and a transmitting coil configured to receive the electrical signal and to transmit the electrical signal to an external antenna;

wherein the sensed physical property is selected from a group consisting of: pressure, stress, strain, or temperature; and wherein the means for converting a sensed physical property into an electrical signal comprises a voltage controlled oscillator.

* * * * *